(12) United States Patent
Tombropoulos et al.

(10) Patent No.: US 12,308,110 B2
(45) Date of Patent: May 20, 2025

(54) SYSTEMS AND METHODS FOR PROCESSING ELECTRONIC IMAGES TO DETERMINE A PLANAR MAPPING

(71) Applicant: HeartFlow, Inc., Redwood City, CA (US)

(72) Inventors: Rhea Tombropoulos, Woodside, CA (US); Gregory R. Hart, Hayden, ID (US); Kathy Yuen, Brisbane, CA (US); Joshua Callebaut, Redwood City, CA (US); John Tran, Austin, TX (US); Jonathan Tang, Redwood City, CA (US); Nrupesh Patel, San Jose, CA (US)

(73) Assignee: Heartflow, Inc., Mountain View, CA (US)

( * ) Notice: Subject to any disclaimer, the term of this patent is extended or adjusted under 35 U.S.C. 154(b) by 403 days.

(21) Appl. No.: 17/661,967

(22) Filed: May 4, 2022

(65) Prior Publication Data

US 2022/0359063 A1 Nov. 10, 2022

Related U.S. Application Data

(60) Provisional application No. 63/201,566, filed on May 5, 2021.

(51) Int. Cl.
*G16H 30/40* (2018.01)
*A61B 5/02* (2006.01)
*G06T 7/00* (2017.01)

(52) U.S. Cl.
CPC ......... *G16H 30/40* (2018.01); *A61B 5/02007* (2013.01); *G06T 7/0012* (2013.01); *G06T 2207/30101* (2013.01)

(58) Field of Classification Search
CPC .. G16H 30/40; A61B 5/02007; G06T 7/0012; G06T 2207/30101; G06T 2210/41;
(Continued)

(56) References Cited

U.S. PATENT DOCUMENTS

2019/0385745 A1\* 12/2019 Lavi ..................... G06T 7/0012
2020/0151874 A1   5/2020 Peterson et al.
(Continued)

FOREIGN PATENT DOCUMENTS

WO     2017114700 A1    7/2017

OTHER PUBLICATIONS

Armin Kanitsar, et al., "Advanced Curved Planar Reformation: Flattening of Vascular Structures," Proceedings of the 14th IEEE Visualization Conference, Oct. 22, 2003, pp. 43-50, The Computer Society, USA.
(Continued)

*Primary Examiner* — Dhaval V Patel
(74) *Attorney, Agent, or Firm* — Bookoff McAndrews, PLLC (57) ABSTRACT

A computer-implemented method for subject-specific two-dimensional modeling of a subject's vasculature may comprise: receiving a subject-specific three-dimensional model of the subject's vasculature, wherein the subject-specific three-dimensional model includes one or more centerlines; determining a two-dimensional viewing plane; determining a projection of the one or more centerlines of the subject-specific three-dimensional model onto the two-dimensional viewing plane; generating one or more models around the one or more centerlines; and generating a two-dimensional image depicting the one or more models.

20 Claims, 8 Drawing Sheets

(58) Field of Classification Search
CPC .......... G06T 2215/06; G06T 2219/004; G06T 2219/008; G06T 15/08; G06T 19/00
See application file for complete search history.

(56) References Cited

U.S. PATENT DOCUMENTS

| | | |
|---|---|---|
| 2021/0209757 A1* | 7/2021 | Min .................. A61B 6/504 |
| 2022/0151580 A1* | 5/2022 | Itu .................. G06T 7/0012 |
| 2022/0164953 A1* | 5/2022 | Gulsun ............. G06T 7/0012 |
| 2022/0254131 A1* | 8/2022 | Lavi .................. A61B 6/467 |

OTHER PUBLICATIONS

Joseph Marino, et al., "Planar Visualization of Treelike Structures", IEEE Transactions on Visualization and Computer Graphics, Jan. 31, 2016, pp. 906-915, IEEE, USA.

P. Eulzer, et al., "Visualizing Carotid Blood Flow Simulations for Stroke Prevention", Eurographics Conference on Visualization (EuroVis), Mar. 29, 2021, 12 pages, Wiley & Sons Ltd.

\* cited by examiner

SYSTEMS AND METHODS FOR PROCESSING ELECTRONIC IMAGES TO DETERMINE A PLANAR MAPPING

CROSS-REFERENCE TO RELATED APPLICATION(S)

This application claims the benefit of priority of U.S. Provisional Patent Application No. 63/201,566, filed May 5, 2021, the entirety of which is incorporated herein by reference.

TECHNICAL FIELD

The disclosure is directed to methods and systems for modeling of subject-specific estimates of blood flow and, more particularly, to methods and systems for visualizing complex vasculature in a single image while retaining information about a vessel topology.

BACKGROUND

Cardiovascular disease is a leading cause of death worldwide. When assessing vascular disease in a subject (e.g., a patient), medical professionals (e.g., physicians) may desire information related to the subject's vasculature, such as vessel size, length, diameter, branching structure, and/or tortuosity. Medical professionals also may also be interested in a presence of any stenoses, disease, imaging artifacts, or stents. Subject-specific three-dimensional reconstructions based on medical imaging data may include some or all of this information. However, specialized software is necessary to view and interact with these three-dimensional models. Such specialized software may not be available to all medical professionals and/or on all devices of a medical professional. Therefore, a need exists for methods and systems for modeling of subject-specific vasculature.

It is to be understood that both the foregoing general description and the following detailed description are exemplary and explanatory only and are not restrictive of the disclosure.

SUMMARY OF THE DISCLOSURE

According to certain aspects of the disclosure, systems and methods are disclosed for two-dimensional modeling A computer-implemented method for subject-specific two-dimensional modeling of a subject's vasculature may comprise: receiving a subject-specific three-dimensional model of the subject's vasculature, wherein the subject-specific three-dimensional model includes one or more centerlines; determining a two-dimensional viewing plane; determining a projection of the one or more centerlines of the subject-specific three-dimensional model onto the two-dimensional viewing plane; generating one or more meshes around the one or more centerlines; and generating a two-dimensional image depicting the one or more meshes.

Furthermore, a system for subject-specific two-dimensional modeling of a subject's vasculature may comprise a data storage device storing instructions for two-dimensional modeling of the subject's vasculature; and a processor configured to execute the instructions to perform operations comprising: receiving a subject-specific three-dimensional model of the subject's vasculature, wherein the subject-specific three-dimensional model includes one or more centerlines; determining a two-dimensional viewing plane; determining a projection of the one or more centerlines of the subject-specific three-dimensional model onto the two-dimensional viewing plane; generating one or more meshes around the one or more centerlines; and generating a two-dimensional image depicting the one or more meshes.

Furthermore, a non-transitory computer-readable medium storing instructions that, when executed by one or more processors, cause the one or more processors to perform a method comprising: receiving a subject-specific three-dimensional model of the subject's vasculature, wherein the subject-specific three-dimensional model includes one or more centerlines; determining a two-dimensional viewing plane; determining a projection of the one or more centerlines of the subject-specific three-dimensional model onto the two-dimensional viewing plane; generating one or more meshes around the one or more centerlines; and generating a two-dimensional image depicting the one or more meshes.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Systems and methods for planar mapping of electronic images may capture information conveyed by a subject-specific three-dimensional model in a single, subject-specific, two-dimensional image, or view. The techniques described herein may map subject-specific three-dimensional vessel model(s) to a single viewing plane, while preserving vessel topology. The subject-specific two-dimensional image may visualize and/or quantify all relevant vessel characteristics from the subject-specific three-dimensional model. The subject-specific two-dimensional image may convey information regarding, for example, vessel size, length, diameter, branching structure, tortuosity, stenoses, disease, imaging artifacts, and/or stents.

The disclosed systems and methods may be performed by a computer processor. The methods and systems may include receiving a three-dimensional model (e.g., a subject-specific three-dimensional model) and defining a viewing plane based on features of the three-dimensional model. After defining the viewing plane, a centerline tree of the three-dimensional model may be mapped to the viewing plane. The mapping may preserve the topology of the centerline tree, including, e.g., a distance between centerline points, a vessel tortuosity, and/or a branching structure. Thereafter, a model (e.g., a mesh) surrounding the centerline tree may be reconstructed in the viewing plane, using, for example, diameters of vessels of the three-dimensional model. Thus, a two-dimensional image (e.g., a subject-specific two-dimensional image) may be constructed or generated that conveys the information of the three-dimensional model. The resulting two-dimensional image may provide advantages over the subject-specific three-dimensional model. For example, the three-dimensional model may require special software for viewing and/or interacting with the three-dimensional model, which may not be available to all relevant parties (e.g., medical professionals, subjects, caregivers, etc.) or may not be available on certain devices (e.g., mobile devices or other devices used remotely). The two-dimensional image may be augmented or annotated to provide various types of information (e.g., comparisons, simulations, labelled images, etc.).

Figure 1:
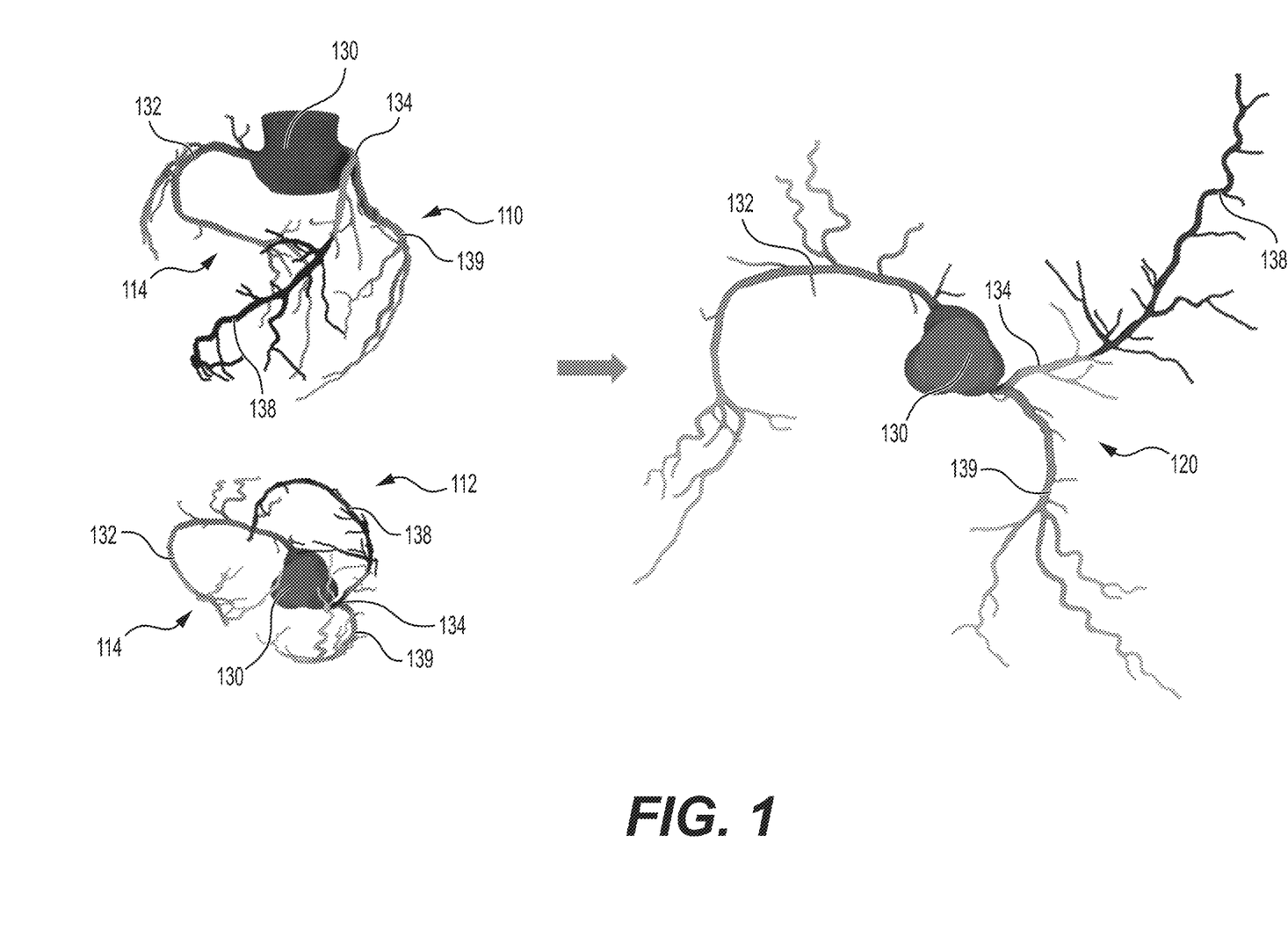
FIG. 1 is a vascular structure rendered into a two-dimensional planar view, according to techniques discussed herein.

FIG. 1 depicts an exemplary frontal view 110 and prone view 112 of an exemplary three-dimensional model 114 of a vasculature. FIG. 1 also depicts an exemplary two-dimensional model 120, which may be created according to the disclosed systems and methods. Further details of two-dimensional model 120 are discussed below, in coordination with the discussion of methods for generating a two-dimensional model, such as two-dimensional model 120.

Three-dimensional model 114 may be generated by using medical images, such as patient-specific images. The images may include images obtained via, for example, Coronary Computed Tomography Angiography ("CCTA") or any other suitable three-dimensional imaging methodologies, such as X-ray, ultrasound, and/or magnetic resonance imaging ("MRI"). Three-dimensional model 114 may include a model of one or more coronary blood vessels (e.g., coronary arteries). Alternatively, three-dimensional model 114 may include one or models of other blood vessels (e.g., blood vessels associated with the brain, coronary veins, peripheral blood vessels, hepatic blood vessels, etc.). Although coronary blood vessels may be referred to herein, such reference is merely for exemplary illustration, and the techniques described herein also apply to other types of blood vessels. Furthermore, the techniques described herein also may apply to other types of bodily structures and are not limited to vasculature. Three-dimensional model 114 may include shading, colors, annotations, or other indicators of blood flow, vessel size, length, diameter, branching structure, tortuosity, stenoses, disease, imaging artifacts, and/or stents. Three-dimensional model 114 may depict a relative size of different vessels and a spatial position of the vessels.

Three-dimensional model 114 may include a three-dimensional mesh surrounding a vessel centerline tree. The three-dimensional mesh may represent surface(s) of one or more vessel(s) (e.g., coronary vessels). The centerlines of the vessel centerline tree may include individual, discrete points that run along center(s) of the vessel mesh. The three-dimensional model may reflect the branching structure of the subject's blood vessels. For each point along the centerline, information relating to different vessel characteristics (such as, for example, distance from ostium, vessel diameter, healthy vessel diameter, percent stenosis, fractional flow reserve (FFR), the presence of plaque or disease, and the presence of artifacts, such as stents or imaging artifacts) may be stored in a computer storage device (e.g., as part of the three-dimensional model or associated with the three-dimensional model).

As shown by comparing frontal view 110 and prone view 112, each view of three-dimensional model 114 may conveys only partial information. Multiple views of three-dimensional model 114 may be necessary in order to understand a structure of the vasculature, as well as the relevant properties of the vasculature, such as those listed above. For example, in each of frontal view 110 and prone view 112, portions of blood vessels may be obscured by other blood vessels. For example, as shown in in frontal view 110 and prone view 112, a first blood vessel 130 (e.g., an aorta) may branch into a second blood vessel 132 (e.g., a right coronary artery) and a third blood vessel 134 (e.g., a left coronary artery). In frontal view 110, portions of third blood vessel 134 may obscure (e.g., be in front of) portions of second blood vessel 132. Details of both second blood vessel 132 and third blood vessel 134 may be difficult to ascertain in such areas of overlap.

Furthermore, by comparing frontal view 110 and prone view 112, it is evident that neither view conveys full information about vessel length, diameter, branching structure, and/or tortuosity. For example, portions of second blood vessel 132 and/or third blood vessel 134 that extend into/out of a screen (e.g., of a display on which three-dimensional model 114 is being viewed) of a particular view 110 or 112 may be particularly difficult to assess from a single view of a three-dimensional model 114. Thus, a two-dimensional image that is merely a single view of a three-dimensional model may fail to deliver all desired information to a viewer, such as a medical professional. As discussed herein, two-dimensional model 120 may address the shortcomings of existing two-dimensional views of vasculature.

Figure 2:
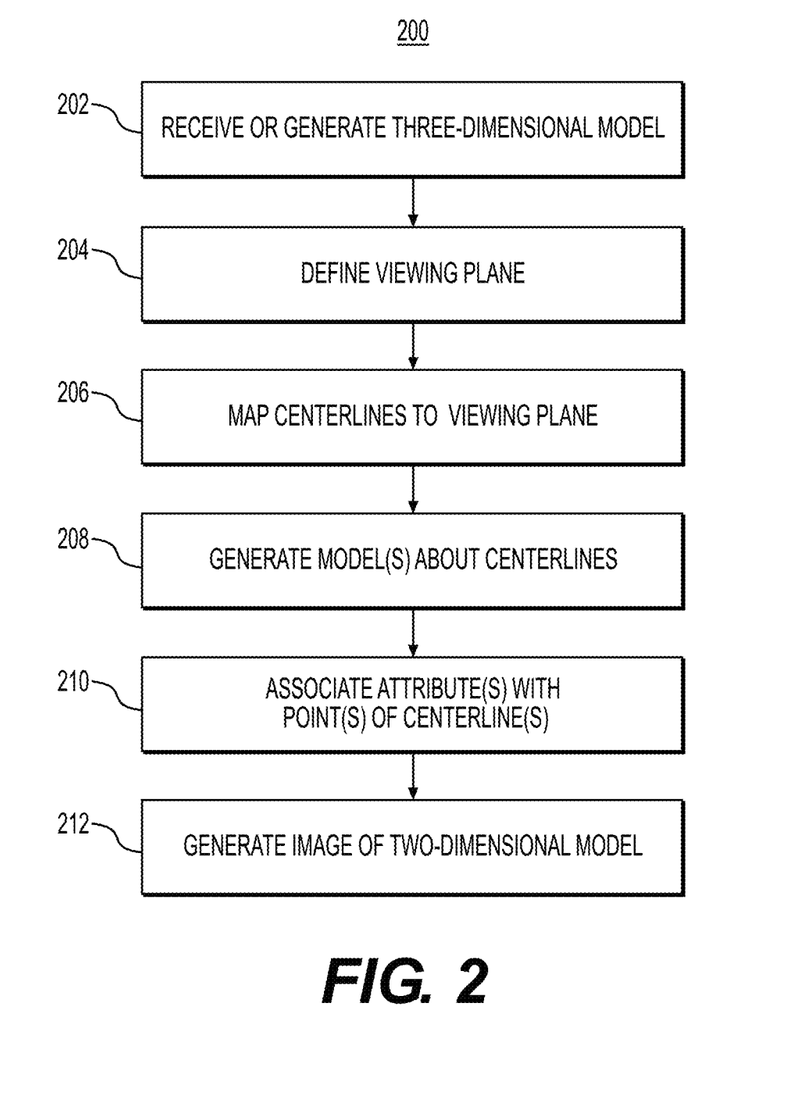
FIG. 2 is a flow-chart depicting an exemplary method for generating a two-dimensional model of a vascular structure.

FIG. 2 depicts a flow diagram of a method 200 for generating two-dimensional model (e.g., image or view view) of vasculature (e.g., a vessel system), while preserving a topology of the vasculature. All of the steps of method 200 may be performed by a computer, as described below with respect to FIG. 7. All of the steps of method 200 may be performed automatically, without human intervention. Step 202 may include receiving or generating three-dimensional model 114 of a vasculature. Three-dimensional 114 model may include, for example, a subject-specific model. Additionally or alternatively, three-dimensional model 114 may include a model of a healthy anatomy and/or a model of a predicted outcome of a treatment (e.g., a placement of a stent or other intervention). The vasculature modeled may include, for example, one or more coronary arteries. In alternatives, step 202 may be omitted or altered, such that step 202 includes receiving medical images but does not include receiving three-dimensional model 114. Where steps below reference three-dimensional model 114, it will be appreciated that such information may be obtained from medical images without generating three-dimensional model 114.

In step 204, a viewing plane may be defined (e.g., automatically defined). The viewing plane may be defined by any suitable convention for a defining a plane, such as by a point on the plane and the normal to the plane. For example, the viewing plane may be defined based on the point where the vessel system (e.g., left or right coronary artery) branches off of the main vessel (e.g., the aorta) and a direction of that main vessel at the branch location. For example, the branching off point may be defined as the center of the ostium where the left or right coronary artery meet the aorta, and the direction of the aorta may be defined as the direction of the aorta centerline at that bifurcation location. The viewing plane may be a plane onto which modeled vessels are projected and/or a plane of an image/two-dimensional model to be generated. With reference to FIG. 2, a viewing plane that faces the same direction as prone view may be chosen to create a two-dimensional model 120. In two-dimensional model 120, the viewing plane may be approximately perpendicular to a centerline of first blood vessel 130 (e.g., an aorta). The viewing plane may be just below (in frontal view 110) or just out of the page from (in prone view) from where second blood vessel 132 and third blood vessel 134 branch from first blood vessel 130. The viewing plane may be chosen so as to include structures (e.g., blood vessels) of interest while not including other structures that are not of interest.

In step 206, point-by-point, each centerline of the centerline tree of three-dimensional model 114 may be mapped onto the viewing plane defined in step 206. For example, if each centerline point has a frame of reference that defines the direction of the centerline at that point, the centerline may be unrolled on the plane in a point-by-point manner. The below equations provide an example of one method for mapping points of the centerline tree onto the viewing plane:
(1) Let $P_0, P_1, \ldots, P_n$ be the consecutive centerline locations in the centerline of the subject-specific three-dimensional model, such that $P_0$ lies on the projection plane (e.g., is the ostium).
(2) Let $d_0, d_1, \ldots, d_n$ depict the directions of the centerline at points $P_0$-$P_n$, respectively in the subject-specific three-dimensional model, such that $d_x$ is a normalized vector representing the tangent to the centerline at position $P_x$.
(3) Let the projected centerline be defined by points $P'_0, P'_1, \ldots, P'_n$ as follows:
 (a) $P'_0 = P_0$
 (b) $P'_x = P'_{(x-1)} + (d'_x * s_x)$, where $d'_x$ is the normalized projection of $d_x$ onto the plane and $s_x$ is the distance between $P_{(x-1)}$ and $P_x$.

Using the exemplary equations above, or other suitable exemplary equations, the centerlines may be projected in a manner that preserves a topology of the centerline tree. For example, points of a given centerline may be separated by a particular distance (in three-dimensional space) in three-dimensional model 114. When the points are projected onto the viewing plane, they may be projected so that they are separated by the same distance (i.e., the distance in three-dimensional space is maintained in the projection). Thus, the projection of step 206 may maintain a length of the centerline and its corresponding blood vessel. An individual utilizing three-dimensional model 114 could rotate three-dimensional model 114 and/or view multiple angles of three-dimensional model 114 in order to apprehend a length of the blood vessels. Two-dimensional model 120 allows this appreciation of a length of the blood vessels in a single, two-dimensional view. Such information may be difficult or impossible to ascertain from looking at a single view of three-dimensional model 114. For example, comparing second blood vessel 132 in prone view 112 and in two-dimensional model 120, second blood vessel 132 may appear longer because certain portions of second blood vessel 132 extend into/out of the page in prone view 112 and, therefore, a length of second blood vessel 132 may not be fully appreciated by viewing prone view 112 in isolation.

Step 206 may be compared to "unwinding" blood vessels of three-dimensional model 114. In step 206, a tortuosity/curvature of the blood vessels may be maintained and depicted in two-dimensional model 120. As illustrated by comparing frontal view 110 of three-dimensional model 114 and two-dimensional model 120, a tortuosity of a first branch 138 of third blood vessel 134 (e.g., a left anterior descending ("LAD") artery) may be determined in the three-dimensional model and preserved in two-dimensional model 120. Looking at prone view 112, a tortuosity of first branch 138 of third blood vessel 134 may be difficult to perceive. In comparison, the projection of step 206 conveys the tortuosity of first branch 138 of third blood vessel 134 in two-dimensional model 120. In some instances, the unwinding/projection of the blood vessels of the tree of the subject-specific three-dimensional model onto a two-dimensional plane may result in some overlap of the blood vessels. In such instances, a relative location of vessels may be adjusted in order to preserve the topology while maximizing visibility of all vessels.

Furthermore, step 206 preserves a branching structure of blood vessels 132, 134 and branches of blood vessels 132, 134. All branching from three-dimensional model 114 may be preserved, and branches may be depicted in an appropriate location. As discussed above, step 206 may preserve a length of the modeled blood vessels by, for example, preserving a spacing between discrete points of centerlines of the blood vessels. Similarly, a position where a branch occurs may be preserved in generating two-dimensional model 120. In an example, a location of a branch in three dimensional-model 114 may relate to one or more discrete points of a centerline of a vessel. The relationship between the discrete points of the centerline and the location of the branch may be preserved in creating two-dimensional model 120. The angle of each branching vessel relative to the vessel from which it branched optionally may also be preserved, approximated, or otherwise represented. The preservation of each branching vessel angle might not be possible in the case of vessel overlaps. In the event an overlap is detected, a deviation from the original angle may be allowed until the vessels no longer overlap either entirely, or by a predetermined margin.

Step 206 may involve applying one or more functions or equations to the blood vessels of three-dimensional model 114 in order to project the blood vessels into the viewing plane. The functions or equations may effectively "unwrap" the blood vessels. These functions or equations may depend upon a chosen plane of view, subject-specific vessel attributes, an area of anatomy, or other factors. Alternatively, a same set of functions or equations may apply to each two-dimensional model 120.

In step 208, one or more models (e.g., vessel meshes, level set, etc.) may be reconstructed around the centerline tree projected in step 206 to generate a "flattened" model of the vasculature. For example, based on stored, individual diameter measurements associated with each centerline point, a three-dimensional levelset (or other volumetric) model may be constructed around the two-dimensional projected centerline. This levelset model may then be converted into, or otherwise used to generate, a three-dimensional vessel mesh (e.g., using a marching cubes algorithm). The vessel mesh may represent, for example, walls of blood vessels. For example, a subject-specific three-dimensional model 114 may include stored information about vessel diameters (i.e., widths) of the vessels of three-dimensional model 114. For example, one or more subject-specific diameters may be stored for each point on the centerline (e.g., a data store may store information about a position of the centerline point, along with an associated vessel diameter at that centerline point). Using subject-specific vessel diameter information, two-dimensional model 120 may depict a diameter of a subject's blood vessels. The subject-specific diameter information may be obtained, for example, by analyzing subject-specific images. Thus, two-dimensional model 120 may maintain vessel size, length, and/or diameter properties of three-dimensional model 114.

Additionally or alternatively, a model (e.g., a mesh) may correspond to a vessel diameter of a healthy subject. In some examples, three-dimensional model 114 may include vessel diameter/widths of a healthy subject. For example, three-dimensional model 114 may model vessel diameter of a healthy subject. Three-dimensional model 114 may additionally or alternatively model a vessel diameter of an actual subject, based on subject-specific medical imaging. In alternatives, information about a vessel diameter/width of a healthy subject may be generated in step 208. Models constructed in step 208 may reflect modeled aspects of three-dimensional model 114, such as the vessel widths of healthy and/or actual subjects, as discussed above.

Additionally or alternatively, a model constructed in step 208 may correspond to a vessel diameter following a simulated intervention (e.g., a treatment such as a stent or other treatment). Portions of the model constructed in step 208 may correspond to vessel diameters of the actual subject and/or a healthy subject, with a diameter of a vessel altered at a particular location of a contemplated or planned intervention. For example, at all locations of a model except for a location of a contemplated intervention, the model may correspond to an actual vessel diameter of a subject. At a location of the contemplated intervention, the model may correspond to a widened diameter to reflect the contemplated intervention.

The models discussed above are merely exemplary, and other models may also be generated. The various exemplary meshes may be combined in any suitable manner. For example, a particular two-dimensional model 120 may include models (e.g., meshes) corresponding to actual subject vessel diameters, healthy vessel diameters, inner lumen wall diameters, outer vessel wall diameters, and/or simulated vessel diameters following a contemplated intervention.

Step 210 may include associating one or more vessel properties or attributes with the discrete points along the vessel centerlines. Such attributes may include, for example, distance from ostium, actual vessel diameter, healthy vessel diameter (e.g., simulated healthy vessel diameter), percent stenosis, presence of plaque, presence of imaging artifacts, presence of stents or other interventions, and/or blood flow values (e.g., computed FFR), simulated interventions, and/or other properties. Step 210 may be performed at any suitable time. For example, step 210 may be performed after step 204, after step 206, or after step 208. In an example, a vector may be associated with each discrete point along the centerlines, and the vector may include the vessel properties. As discussed below, the vessel attributes may be incorporated into two-dimensional images (e.g., via annotations) to depict attributes of the blood vessels and/or other features of the vascularity.

Step 212 may include outputting a two-dimensional image of two-dimensional model 120. In examples, step 212 may include outputting only one image depicting the subject's vasculature at a given area of interest, and all relevant information may be conveyed by the single image. Step 212 may include adding or including annotations related to the attributes of step 210. Step 212 may additionally include receiving inputs from an operator (e.g., a medical professional) regarding which information to include in the two-dimensional image. Different vessel properties may be included, depending on inputs from the operator. Alternatively or additionally, step 212 may include generating a default two-dimensional image including a default set of vessel properties. In examples, an operator may make alterations to the default image having the default set of vessel properties, and step 212 may include receiving inputs reflecting selections from the operator of which alterations to include. For example, step 212 may include receiving inputs reflecting a simulated treatment, a desire to view vessel diameters of a healthy patient, or other selections of the operator.

As shown in FIG. 1, two-dimensional model 120 may include indications of an FFR at different locations of the blood vessels. For example, as shown in FIG. 1, three-dimensional model 114 and two-dimensional model 120 each may include shading to indicate a calculated FFR. In the exemplary two-dimensional model 120, portions of first branch 138 of second blood vessel may have a lower FFR than other blood vessels, including a second branch 139 of third blood vessel 134 (e.g., a left circumflex artery) and second blood vessel 132. The blood vessel attributes (e.g., FFR values) from three-dimensional model 114 are also incorporated into two-dimensional model 120, as discussed above.

Described below are various exemplary images that can be generated to depict two-dimensional models generated according to the above-described methods. Although the examples of FIGS. 3-6 depict stenoses, it will be appreciated that such depictions are merely exemplary, and the two-dimensional models described herein may be generated or annotated in order to reflect a wide variety of metrics or other characteristics of interest. For example, images of two-dimensional models may be annotated or otherwise generated to depict metrics/characteristics such as vessel volume, tissue perfusion, FFR, flow velocity, treatment modeling/prediction, disease progression, predictions of disease course, comparisons to characteristics of a broader population, or other types of metrics or characteristics).

Figure 3:
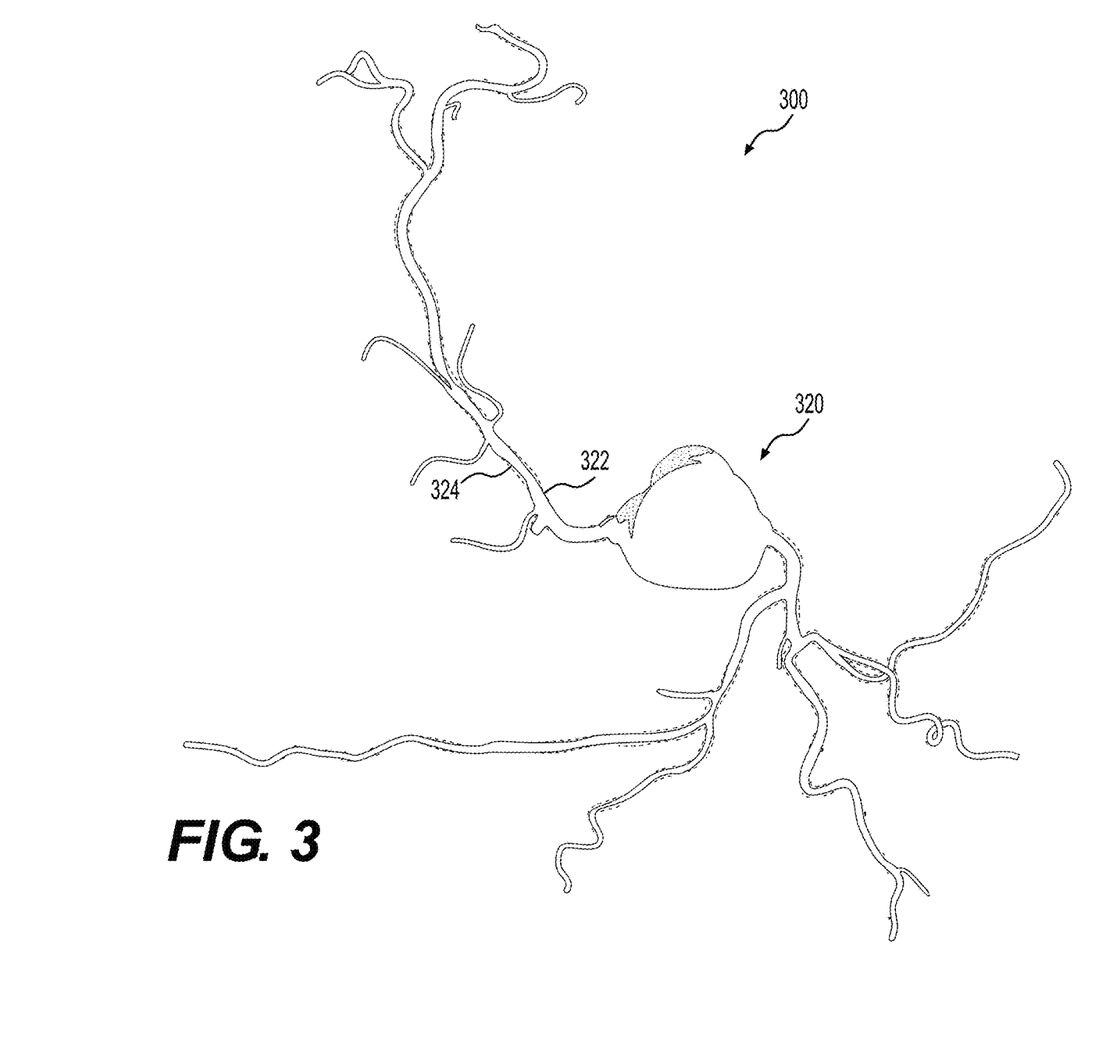
FIG. 3 depicts a two-dimensional image comparing a subject-specific vascular model to a simulated healthy vascular model.

FIG. 3 shows an image 300 of another two-dimensional model 320. Two-dimensional model 320 may depict blood vessels of a same subject as model 120 or may depict blood vessels of a different subject. As shown in FIG. 3, two-dimensional model 320 may include a first mesh 322 (solid lines) depicting an actual diameter of blood vessels (e.g., coronary blood vessels) of two-dimensional model 320. Two-dimensional model 320 also may include a second mesh 324 (broken lines) depicting a diameter of blood vessels of a healthy subject. The centerlines of two-dimensional model 320 may be based on the subject's actual blood vessels. The tortuosity, branching structure, etc. of two-dimensional model 320 also may be based on the actual structure of the subject's blood vessels. The second mesh (broken lines) may be generated, for example, by applying population-based data to the subject-specific centerline tree. The image of FIG. 3 may include color-coding to indicate an actual diameter of a subject's vessel and/or a diameter of a healthy vessel.

In alternatives, image 300 depicted in FIG. 3 may include two two-dimensional models, one overlaid over the other. For example, a first subject-specific two-dimensional model may depict actual diameters of the subject's blood vessels.

A second two-dimensional model may depict diameters of healthy blood vessels. The second model may be subject-specific because it depicts a length, tortuosity, branching, etc. of the subject, although it depicts diameters of healthy blood vessels. The first model may be laid over the second model.

As shown in FIG. 3, first mesh 322 may be narrower than second mesh 324 at certain locations. These locations may correspond to stenoses of the subject's vasculature. Image 300 may allow a user (e.g., medical professional or patient) to appreciate, in one single two-dimensional image, how a subject's vasculature may differ from a healthy vasculature due to, e.g., narrowing of blood vessels. Image 300 (and the other images describe herein) also may allow the user to appreciate how locations of stenoses relate to vascular structure, including blood vessels downstream of a stenosis.

Figure 4:
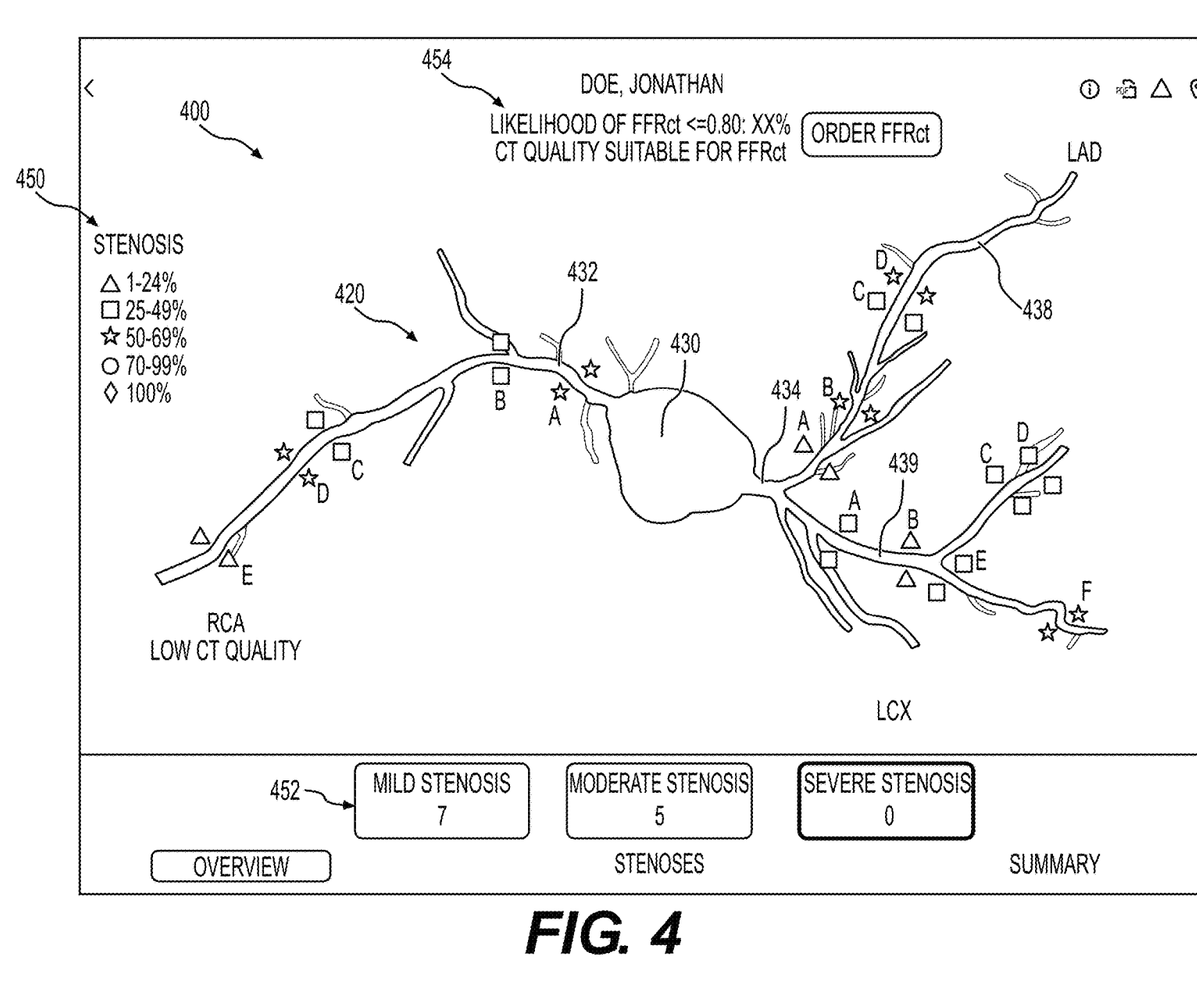
FIGS. 4-6 are two-dimensional images depicting information about stenoses of a subject's blood vessels, according to an exemplary embodiment of the present disclosure.

FIG. 4 depicts another exemplary image 400 of a two-dimensional model 420. Model 420 may depict blood vessels of a same subject as models 120 and/or 320 or of a different subject than models 120 and 320. Model 420 may model a first blood vessel 430 (e.g., an aorta), which may branch into a second blood vessel 432 (e.g., a right coronary artery) and a third blood vessel 434 (e.g., a left coronary artery). Third blood vessel 434 vessel may branch into a first branch 438 (e.g., a LAD artery) and a second branch 439 (e.g., a left circumflex artery).

Image 400 may include annotations (see letters A-E of second blood vessel 432, letters A-D of first branch 438, and letters A-F of second branch 439). The letters may denote locations along a vessel. Each letter may include a category denoted by, for example, a color or symbol. The color or symbol may denote an amount of stenosis. For example, as shown in a key 450, different colors and/or symbols may denote an amount of stenosis (e.g., 1-24%, 24-49%, 50-69%, 70-99%, and/or 100%). In alternatives, the annotations may reflect other attributes (e.g., FFR, difference between vessel width and healthy vessel width, simulated interventions, artifacts, etc.)

Key 450 may include a summary 452 of stenosis by category. For example, 24-49% may correspond to a mild stenosis. 50-69% may correspond to a moderate stenosis. Above 70% may correspond to a severe stenosis. Summary 452 may provide a total number of stenosis in each category. The values provided above are merely exemplary, and suitable values or ranges may be utilized. A header 454 may include a button that an operator may select in order to order tests, such as an FFRcT. Header 454 may also include an indicator of whether imaging data (e.g., CT data) is of sufficient quality to order a specified test or set of tests. Header 454 also may provide a prediction about an outcome of the test (e.g., a percentage likelihood that an FFRcT has a value below a threshold, such as 0.80.

Figure 5A:
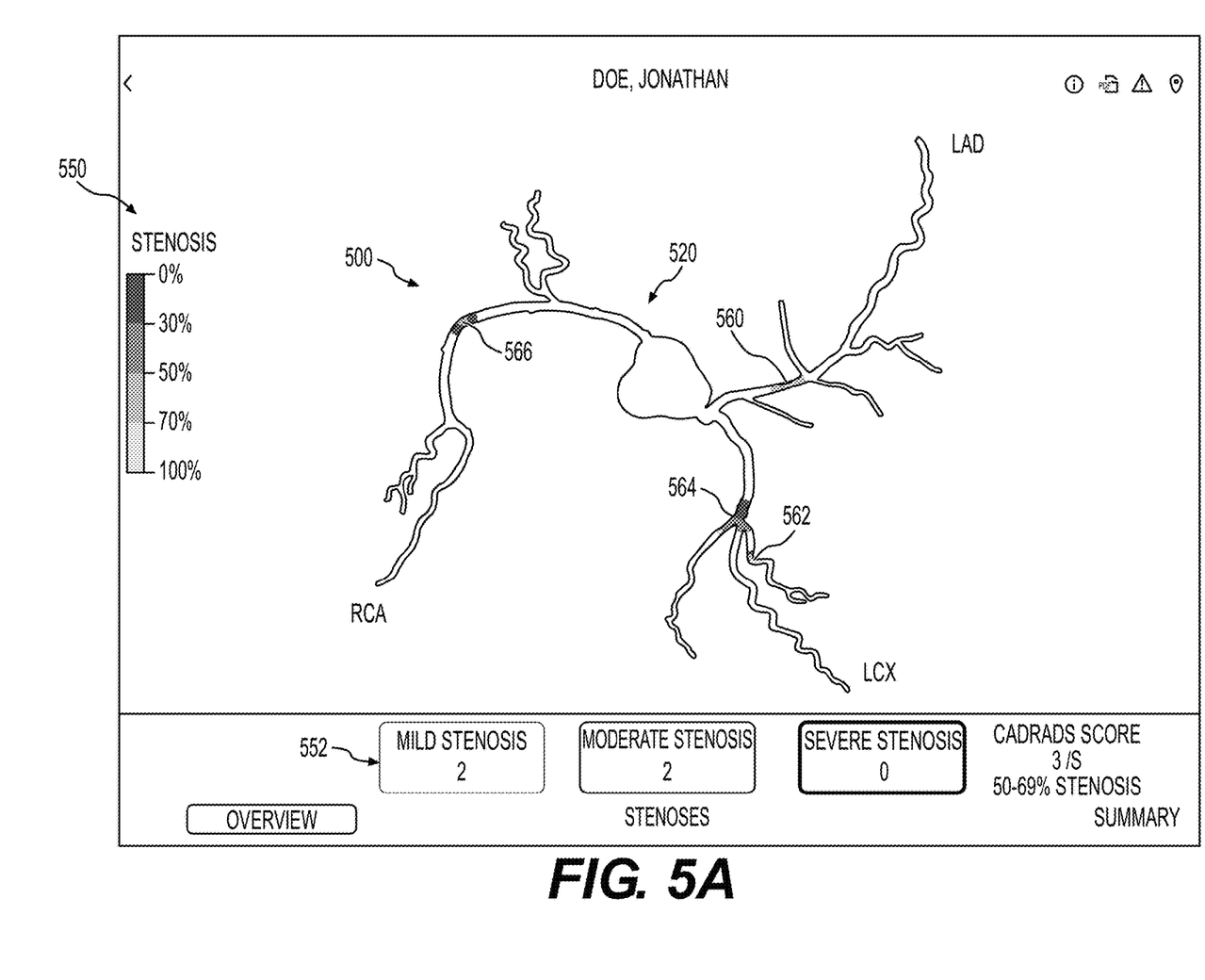

FIG. 5A depicts an image 500 of a two-dimensional model 520. Model 520 may depict blood vessels of a same subject as models 120, 320 and/or 420 or of a different subject than models 120, 320, and/or 420 As shown in FIG. 5A, image 500 of model 520 may include a key 550 that defines color gradations (or shade gradations) of model 520 that correspond to certain percentages of stenosis. Although depicted as having a white background for ease of illustration, image 500 may, for example, have a dark-colored background. The shades of key 550 are also chosen for convenience and ease of illustration, and the shades or values of key 550 may be any desired shades or values. Example stenoses 560, 562, 564, 566 are labeled in FIG. 5A. The exemplary labeled stenoses are non-exclusive, and model 520 may model other stenoses that are not labeled.

Image 500 may include a summary 552 of stenoses by category. For example, stenosis of model 520 may be grouped by category (e.g., mild, moderate, or severe) or according to other metrics. In categorizing the stenoses, a computer may compare stenoses to one or more thresholds or perform other calculations or analyses. For example, as shown in summary 552, the modeled vasculature may include two mild stenoses and two moderate stenoses. Summary 552 may also include a coronary artery disease reporting and data system ("CADRADS") score. For example, the vasculature modeled in model 520 may have a CADRADS score of 3, corresponding to 50-69% stenosis (moderate stenosis).

Figure 5B:
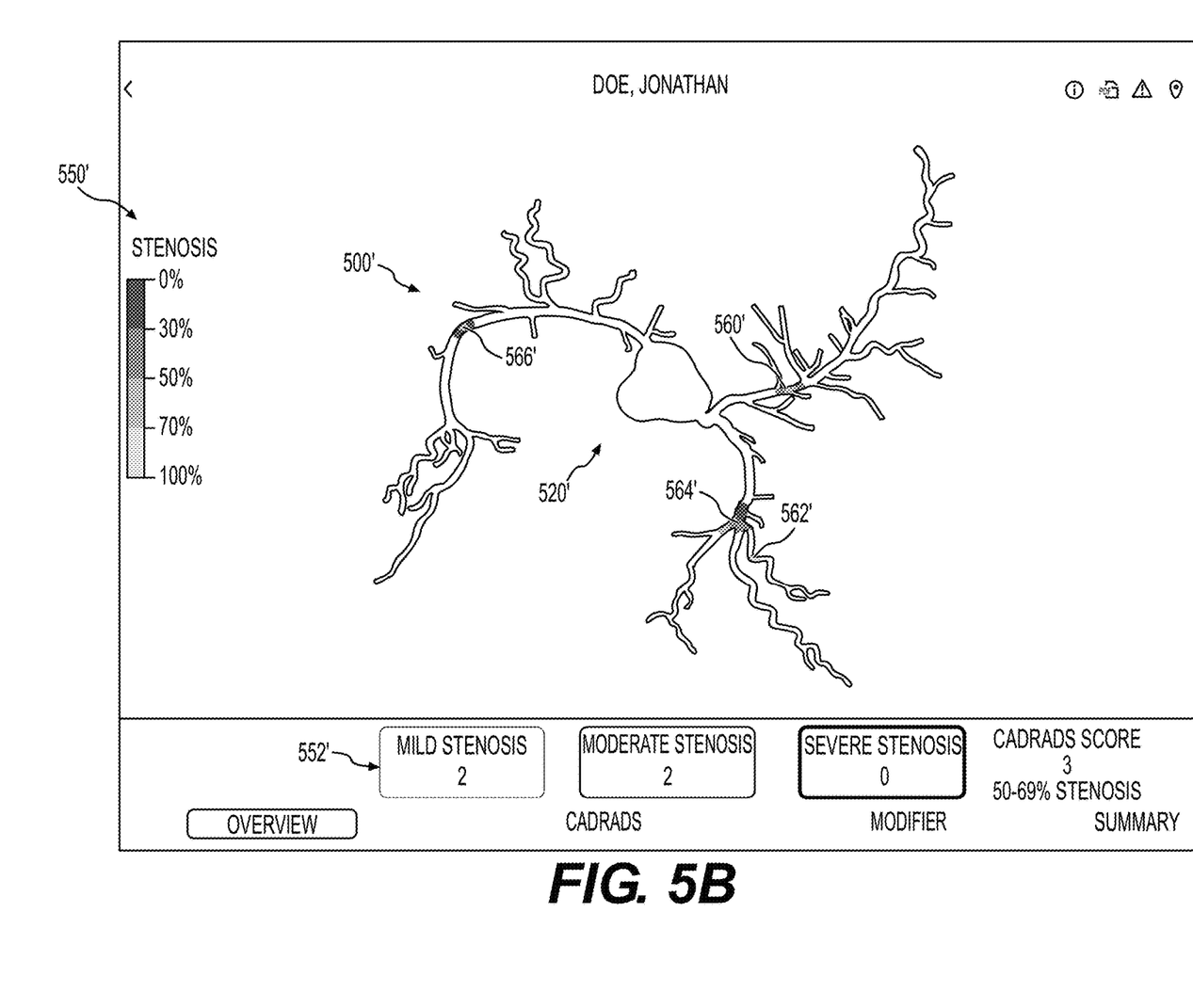

FIG. 5B depicts an image 5500' of a two-dimensional model 5520'.' Model 520' may depict blood vessels of a same subject as models 120, 320, 420, and/or 520, or of a different subject than models 120, 320, 420, and/or 520 As shown in FIG. 5B, image 5500' of model 520' may include a key 550' that defines color gradations (or shade gradations) of model 520' that correspond to certain percentages of stenosis. Although depicted as having a white background for ease of illustration, image 500' may, for example, have a dark-colored background. Vasculature of model 520' may be colored, for example, light blue. The shades of key 550' are also chosen for convenience and ease of illustration, and the shades or values of key 550' may be any desired shades or values. For example, colors of key 550' may range from blue (less stenosis) to yellow (more stenosis). Example stenoses 560,' 562,' 564,' 568' are labeled in FIG. 5B. The exemplary labeled stenoses are non-exclusive, and model 520' may model other stenoses that are not labeled.

Key 550' may include a summary 552' of stenoses by category. For example, stenosis of model 520' may be grouped by category (e.g., mild, moderate, or severe) or according to other metrics. In categorizing the stenoses, a computer may compare stenoses to one or more thresholds or perform other calculations or analyses. For example, as shown in summary 552,' the modeled vasculature may include two mild stenoses and two moderate stenoses. Summary 552 may also include a CADRADS score. For example, the vasculature modeled in model 520' may have a CADRADS score of 3, corresponding to 50-69% stenosis (moderate stenosis).

Images 400, 500, 500' each may allow a user (e.g., a medical professional or a subject) to appreciate a vascular structure, presence of stenoses, and severity of stenoses in a single, two-dimensional image. The user may make selections to select between different types of images (e.g., image 500 vs. image 500') depending on preferences and/or attributes of a particular subject. The user may use the information obtained from any of the images described herein in order to plan treatments or to determine whether further tests should be ordered. It will be appreciated that the annotations shown in FIGS. 1 and 3-5B are merely exemplary, and other annotations reflecting other attributes may additionally or alternatively be depicted.

Figure 6:
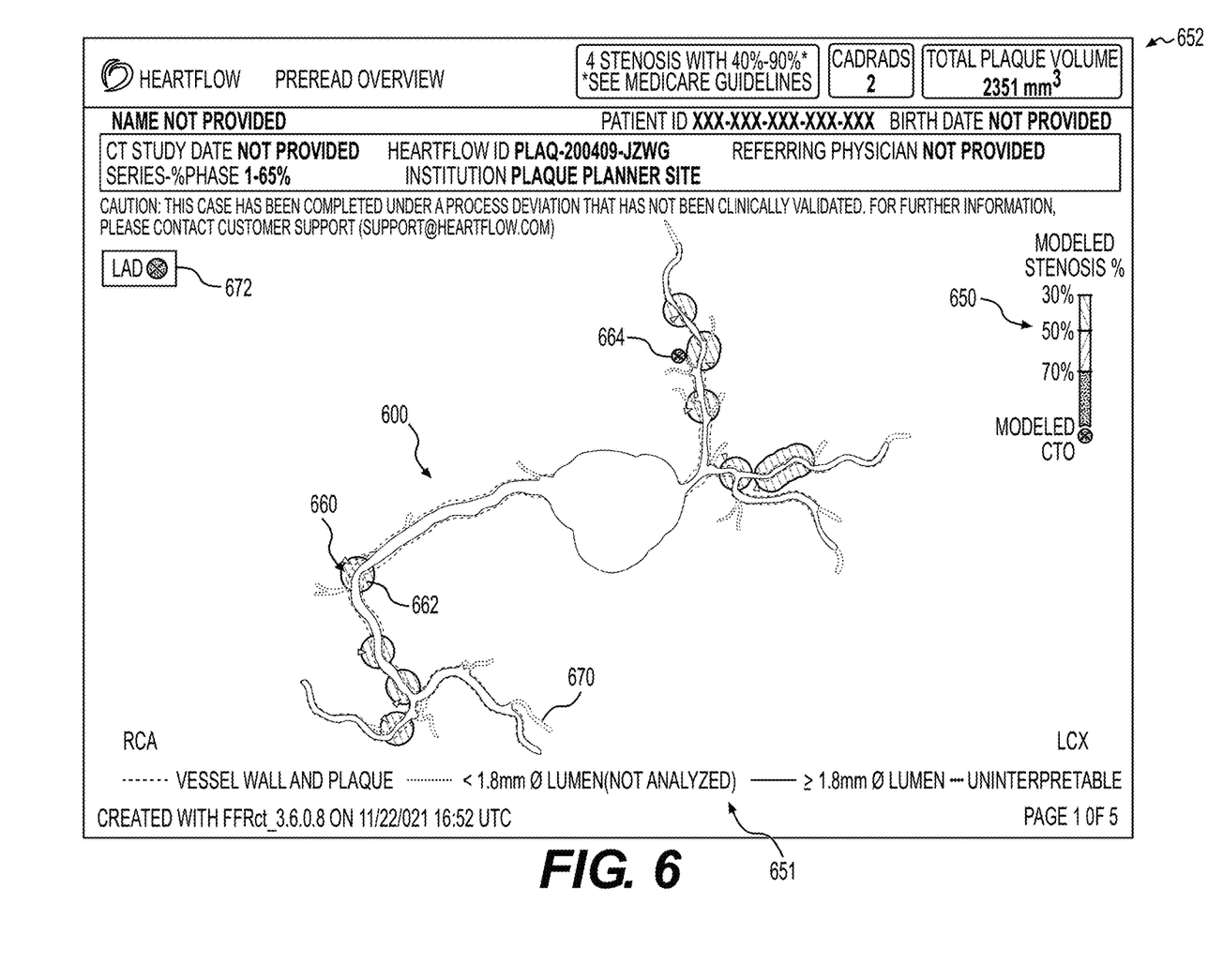

FIG. 6 depicts an image 600 of a two-dimensional model 620. Model 620 may depict blood vessels of a same subject as models 120, 320, 420, 520, or 520' or of a different subject than models 120, 320, 420, 520, or 520'. As shown in FIG. 6, image 600 of model 620 may include a stenosis key 650 that defines color gradations (or shade gradations) of model 620 that correspond to certain percentages of stenosis. Although image 600, including stenosis key 650, are depicted in black and white for ease of illustration, it will be appreciated that all or portions of image 600 may be in color. For example, in stenosis key 650, a stenosis percentage of 30%-50% may have a first color, a stenosis percentage of 50%-70% may have a second color, and a stenosis percentage of 70% or higher may have a third color. A symbol, such as a circle with an "X" as shown in FIG. 6, may represent a chronic total occlusion ("CTO"). Image 600 may also include a lumen key 651. Although lumen key 651 denotes different lumen features with broken and solid lines, it will be appreciated that, if image 600 is in color, lumen key 651 may denote lumen features with different colors. As shown in lumen key 651, a solid line may represent a lumen having a diameter above or equal to a certain threshold (e.g., above 1.88 mm). A first type of broken line may represent a vessel wall, and a space between the first type of broken line and the solid line may represent a plaque. A second type of broken line may represent a lumen having a diameter smaller than the threshold (e.g., below 1.88 mm) (e.g., vessel 670 of image 600). Although not depicted in FIG. 6, as shown in lumen key 651, image 600 may also denote uninterpretable findings.

Shaded areas, such as area 662 may denote a stenosis 660, as indicated in stenosis key 650. The shaded areas may be approximately circular, oblong, or any suitable shape. Multiple shaded areas indicating stenoses may overlap one another. Arrowheads within shaded areas (e.g., the arrowhead within area 660) may denote areas of particular interest (e.g., areas of particular narrowing). A symbol (e.g., a circle with an "X", as shown in stenosis key 650) may represent a CTO 664. A summary 652 may provide an overview of findings, such as, e.g., a number of stenoses within a particular range, such as 40%-90%, a CADRADS score, a total plaque volume, or other relevant values or analyses. Image 600 may also include one or more labels, such as label 672, indicating the LAD. As shown in image 600, label 672 may include a symbol corresponding to the symbol in stenosis key 650 for a CTO, to indicate a CTO in the vasculature corresponding to the label.

Although FIGS. 3-6 may depict stenoses, it will be appreciated that the systems and methods described herein may be utilized to depict two-dimensional models pertaining to any suitable metric or other characteristic (e.g., vessel volume, tissue perfusion, FFR, flow velocity, treatment modeling, or other types of metrics or characteristics).

Any of the methods and techniques discussed above may incorporate machine learning techniques. For example, machine learning may be utilized to define a viewing plane and/or to map centerline(s) of vessel(s). In an example, a trained machine learning model may be used to determine an appropriate projection type of a centerline tree of a three-dimensional model (e.g., how to "unwind" the centerlines to convey a tortuosity of a vessel tree while allowing for a two-dimensional projection). A type of machine learning technique is not limited and may include any machine learning technique that is known or becomes known. The machine learning model may be trained by providing the machine learning with population patient data and models.

Using the techniques described herein, a single image may be generated, which represents a subject-specific atlas of an individual's vasculature. As discussed with respect to FIG. 2, projecting a three-dimensional vessel onto a two-dimensional image may preserve the vessel topology such that vessel segment lengths, diameters, twists, turns, and branching structure are maintained in a planar representation. Furthermore, because for each discrete point along the vessel centerline, myriad properties (i.e., attributes) of the vessel (e.g., actual diameter, simulated healthy diameter, percent stenosis, presence of plaque, presence of imaging artifacts, presence of stents, computed FFR (e.g., FFRcT), etc.) may be stored, the two-dimensional models may be annotated to provide useful information to a viewer, as discussed with respect to FIGS. 1-6. The techniques described herein may be particularly useful for viewing images on mobile devices and/or for screening subjects for further treatment and/or analysis. For example, an environment (e.g., the environment of FIG. 7, below) may present a two-dimensional image prepared according to the techniques described herein as a first, snapshot image after obtaining subject-specific images. The user may then determine whether or not to pursue further analysis, including obtaining access to three-dimensional models.

Techniques discussed herein may apply to the display of a subject's vasculature, including the display of vasculature where the presence of disease is highlighted. Techniques discussed herein may further be applied for the display of healthy vasculature, for example a simulated healthy vasculature if disease were not present. The displayed model may also be used to simulate the outcome of one or more interventions, including medication, stenting, bypass or other surgical procedure, diet, exercise, etc. Disease progression may further be displayed or simulated. Techniques discussed herein may further be used with the annotation of an anatomical model with specific statistics related to the vasculature, such as length of vessels, length of stenoses, size of vessels, percent stenosis, presence of various types of disease, imaging artifacts, and/or simulated fractional flow reserve (FFR) results along the vessel. A user may utilize the images described herein in order to plan treatments or to determine whether to order additional testing. Alternatively, method 200 may include automatically generating treatment recommendations, which may be displayed on the exemplary images described herein. Thus, the techniques described herein constitute improvements to existing modeling techniques.

Any method discussed in this disclosure that is understood to be computer-implementable, including the methods associated with FIGS. 1-6, may be performed by one or more processors of a computer system. A step of a method performed by one or more processors may also be referred to as an operation.

Figure 7:
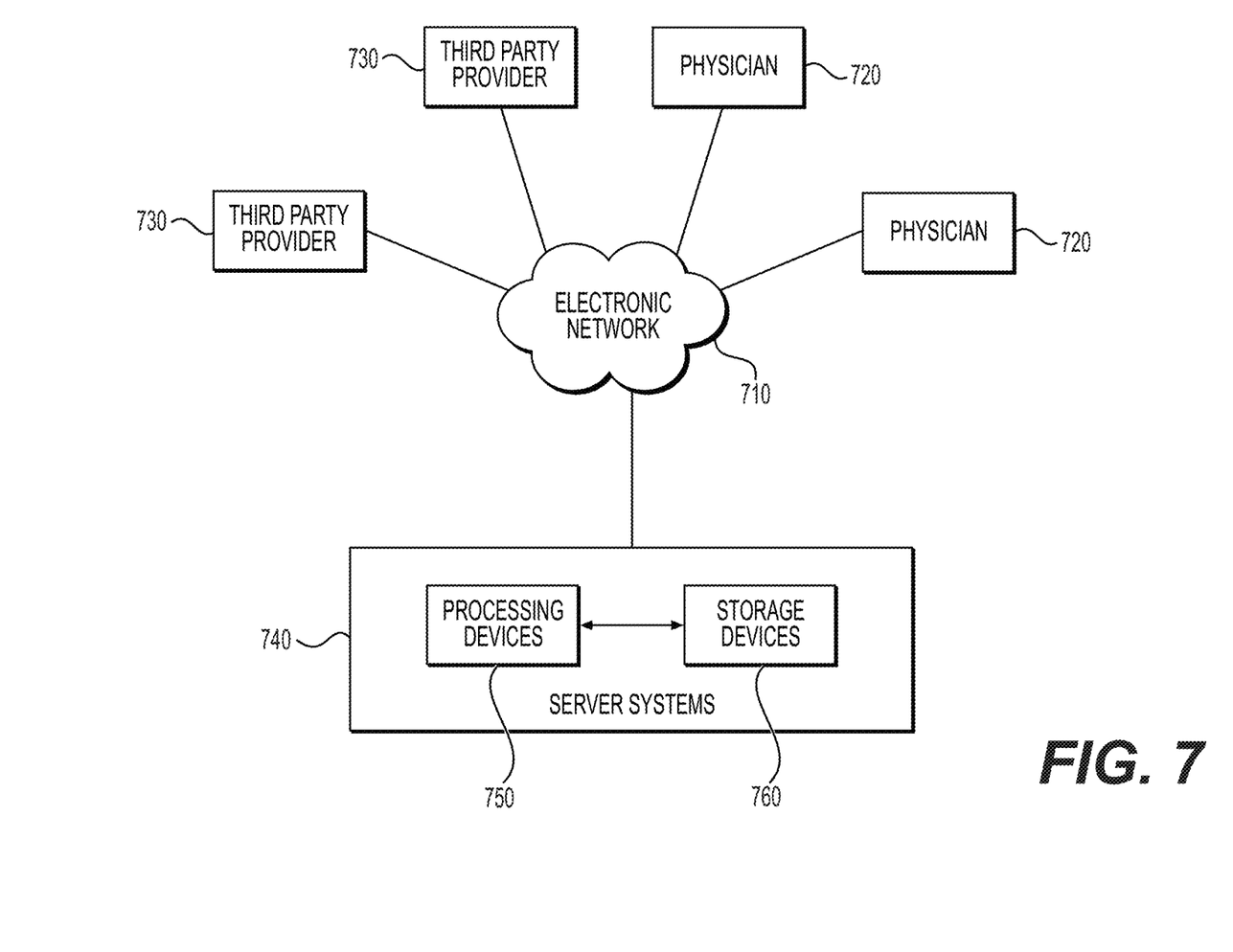
FIG. 7 depicts a computer environment for performing the techniques of FIG. 2 and generating the images of FIGS. 1-6.

FIG. 7 depicts an example of an environment in which such a computer system may be implemented as server systems 740. In addition to server systems 740, the environment of FIG. 7 further includes a plurality of physicians 720 and third party providers 730, any of which may be connected to an electronic network 710, such as the Internet, through one or more computers, servers, and/or handheld mobile devices. In FIG. 1, physicians 720 and third party providers 730 may each represent a computer system, as well as an organization that uses such a system. For example, a physician 720 may be a hospital or a computer system of a hospital.

Physicians 720 and/or third party providers 730 may create or otherwise obtain medical images, such as images of the cardiac, vascular, and/or organ systems, of one or more patients. Physicians 720 and/or third party providers 730 may also obtain any combination of patient-specific information, such as age, medical history, blood pressure, blood viscosity, and other types of patient-specific information. Physicians 720 and/or third party providers 730 may transmit the patient-specific information to server systems 740 over the electronic network 710.

Server systems 740 may include one or more storage devices 760 for storing images and data received from physicians 720 and/or third party providers 730. The storage devices 760 may be considered to be components of the memory of the server systems 740. Server systems 740 may also include one or more processing devices 750 for processing images and data stored in the storage devices and for performing any computer-implementable process described in this disclosure. Each of the processing devices 750 may be a processor or a device that include at least one processor.

In some embodiments, server systems 740 may have a cloud computing platform with scalable resources for computations and/or data storage, and may run an application for performing methods described in this disclosure on the cloud computing platform. In such embodiments, any outputs may be transmitted to another computer system, such as a personal computer, for display and/or storage.

Other examples of computer systems for performing methods of this disclosure include desktop computers, laptop computers, and mobile computing devices such as tablets and smartphones.

The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or another type of processing unit.

A computer system, such as server systems 740, may include one or more computing devices. If the one or more processors of the computer system is implemented as a plurality of processors, the plurality of processors may be included in a single computing device or distribute among a plurality of computing devices. If a computer system comprises a plurality of computing devices, the memory of the computer system may include the respective memory of each computing device of the plurality of computing devices.

In general, a computing device may include processor(s) (e.g., CPU, GPU, or other processing unit), a memory, and communication interface(s) (e.g., a network interface) to communicate with other devices. Memory may include volatile memory, such as RAM, and/or non-volatile memory, such as ROM and storage media. Examples of storage media include solid-state storage media (e.g., solid state drives and/or removable flash memory), optical storage media (e.g., optical discs), and/or magnetic storage media (e.g., hard disk drives). The aforementioned instructions (e.g., software or computer-readable code) may be stored in any volatile and/or non-volatile memory component of memory. The computing device may, in some embodiments, further include input device(s) (e.g., a keyboard, mouse, or touchscreen) and output device(s) (e.g., a display, printer). The aforementioned elements of the computing device may be connected to one another through a bus, which represents one or more busses. In some embodiments, the processor(s) of the computing device includes both a CPU and a GPU.

Instructions executable by one or more processors may be stored on a non-transitory computer-readable medium. Therefore, whenever a computer-implemented method is described in this disclosure, this disclosure shall also be understood as describing a non-transitory computer-readable medium storing instructions that, when executed by one or more processors, configure or cause the one or more processors to perform the computer-implemented method. Examples of non-transitory computer-readable medium include RAM, ROM, solid-state storage media (e.g., solid state drives), optical storage media (e.g., optical discs), and magnetic storage media (e.g., hard disk drives). A non-transitory computer-readable medium may be part of the memory of a computer system or separate from any computer system. An "electronic storage device" may include any of the non-transitory computer-readable media described above.

It should be appreciated that in the above description of exemplary embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the disclosure, and it is intended to claim all such changes and modifications as falling within the scope of the disclosure. For example, functionality may be added or deleted from the block diagrams and operations may be interchanged among functional blocks. Steps may be added or deleted to methods described within the scope of the present disclosure.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted.

We claim:

1. A computer-implemented method for subject-specific two-dimensional modeling of a subject's vasculature, comprising:
   receiving a subject-specific three-dimensional model of the subject's vasculature, wherein the subject-specific three-dimensional model includes one or more centerlines;
   determining a two-dimensional viewing plane;
   determining a projection of the one or more centerlines of the subject-specific three-dimensional model onto the two-dimensional viewing plane, wherein each of the one or more centerlines of the subject-specific three-dimensional model includes a plurality of discrete points, and wherein determining the projection of the one or more centerlines includes maintaining distances between the plurality of discrete points of respective centerlines of the subject-specific three-dimensional model;
generating one or more meshes around the one or more centerlines; and
generating a two-dimensional image depicting the one or more meshes.

2. The method of claim 1, further comprising associating one or more vessel attributes with one or more points of one of the one or more centerlines.

3. The method of claim 2, wherein the one or more vessel attributes include diameter, healthy diameter, percent stenosis, presence of plaque, presence of imaging artifacts, presence of stents, or FFR.

4. The method of claim 2, wherein the two-dimensional image includes one or more annotations relating to the one or more vessel attributes.

5. The method of claim 2, wherein associating the one or more vessel attributes include attributes of the subject-specific three-dimensional model.

6. The method of claim 1, wherein the two-dimensional image preserves a size, length, diameter, branching structure, or tortuosity of the subject-specific three-dimensional model.

7. The method of claim 1, wherein the subject-specific three-dimensional model is based on one or more subject-specific medical images.

8. The method of claim 1, wherein the two-dimensional image depicts only one view of the subject's vasculature.

9. The method of claim 1, wherein determining the two-dimensional viewing plane comprises:
    determining a location of a central vessel of the subject's vasculature;
    determining an ostium location of one or more branching vessels extending from the central vessel; and
    assigning the two-dimensional viewing plane based on the ostium location.

10. The method of claim 1, wherein the projection maintains a determined distance between points along the one or more centerlines, vessel tortuosity, and/or branching structure.

11. A system for subject-specific two-dimensional modeling of a subject's vasculature, comprising:
    a data storage device storing instructions for two-dimensional modeling of the subject's vasculature; and
    a processor configured to execute the instructions to perform operations comprising:
        receiving a subject-specific three-dimensional model of the subject's vasculature, wherein the subject-specific three-dimensional model includes one or more centerlines;
        determining a two-dimensional viewing plane;
        determining a projection of the one or more centerlines of the subject-specific three-dimensional model onto the two-dimensional viewing plane, wherein each of the one or more centerlines of the subject-specific three-dimensional model includes a plurality of discrete points, and wherein determining the projection of the one or more centerlines includes maintaining distances between the plurality of discrete points of respective centerlines of the subject-specific three-dimensional model;
        generating one or more meshes around the one or more centerlines; and
        generating a two-dimensional image depicting the one or more meshes.

12. The system of claim 11, wherein the operations further comprise associating one or more vessel attributes with one or more points of one of the one or more centerlines.

13. The system of claim 12, wherein the one or more vessel attributes include diameter, healthy diameter, percent stenosis, presence of plaque, presence of imaging artifacts, presence of stents, or FFR.

14. The system of claim 11, wherein the two-dimensional image preserves a size, length, diameter, branching structure, or tortuosity of the subject-specific three-dimensional model.

15. The system of claim 11, wherein the subject-specific three-dimensional model is based on one or more subject-specific medical images.

16. A non-transitory computer-readable medium storing instructions that, when executed by one or more processors, cause the one or more processors to perform a method comprising:
    receiving a subject-specific three-dimensional model of a subject's vasculature, wherein the subject-specific three-dimensional model includes one or more centerlines;
    determining a two-dimensional viewing plane;
    determining a projection of the one or more centerlines of the subject-specific three-dimensional model onto the two-dimensional viewing plane, wherein each of the one or more centerlines of the subject-specific three-dimensional model includes a plurality of discrete points, and wherein determining the projection of the one or more centerlines includes maintaining distances between the plurality of discrete points of respective centerlines of the subject-specific three-dimensional model;
    generating one or more meshes around the one or more centerlines; and
    generating a two-dimensional image depicting the one or more meshes.

17. The non-transitory computer-readable medium of claim 16, wherein the method further comprises associating one or more vessel attributes with one or more points of one of the one or more centerlines.

18. The non-transitory computer-readable medium of claim 17, wherein the one or more vessel attributes include diameter, healthy diameter, percent stenosis, presence of plaque, presence of imaging artifacts, presence of stents, or FFR.

19. The system of claim 11, wherein determining the two-dimensional viewing plane comprises:
    determining a location of a central vessel of the subject's vasculature;
    determining an ostium location of one or more branching vessels extending from the central vessel; and
    assigning the two-dimensional viewing plane based on the ostium location.

20. The non-transitory computer-readable medium of claim 16, wherein determining the two-dimensional viewing plane comprises:
    determining a location of a central vessel of the subject's vasculature;
    determining an ostium location of one or more branching vessels extending from the central vessel; and
    assigning the two-dimensional viewing plane based on the ostium location.

* * * * *